United States Patent [19]

Heller et al.

[11] Patent Number: 5,013,821

[45] Date of Patent: May 7, 1991

[54] ORTHO AND THIO-ORTHO ESTER POLYMER

[75] Inventors: Jorge Heller, Woodside; Steve Y. W. Ng, San Francisco; Donald W. H. Penhale, Menlo Park, all of Calif.

[73] Assignee: Pharmaceutical Delivery Systems, Inc., Menlo Park, Calif.

[21] Appl. No.: 348,059

[22] Filed: Jun. 15, 1989

[51] Int. Cl.$^5$ ............................................. C08G 67/00
[52] U.S. Cl. ................................... 528/376; 528/364; 528/392
[58] Field of Search ..................... 528/376, 392, 364

[56] References Cited

U.S. PATENT DOCUMENTS

| | | | |
|---|---|---|---|
| 2,996,516 | 8/1961 | Guest et al. | 528/376 |
| 4,093,709 | 6/1978 | Choi et al. | 424/19 |
| 4,131,648 | 12/1978 | Choi et al. | 424/22 |
| 4,139,344 | 2/1979 | von der Eltz | 8/21 |
| 4,180,646 | 12/1979 | Choi et al. | 528/153 |
| 4,304,767 | 12/1981 | Heller et al. | 424/78 |

Primary Examiner—Harold D. Anderson
Attorney, Agent, or Firm—Dianne E. Reed

[57] ABSTRACT

Biodegradable ortho'ester polymers based on mono- and poly-thiols are provided that are useful for making biodegradable sustained release agent dispensers and which contain at least one of the mer units (I), (II), (III) or (IV)

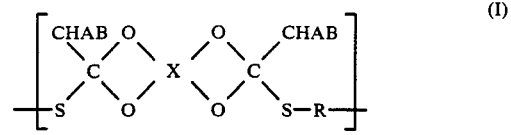

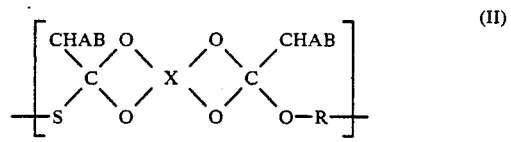

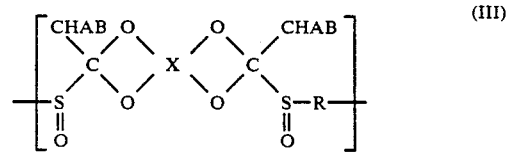

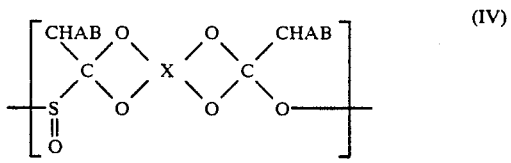

wherein X is a quadrivalent organic grouping, A and B are independently selected from the group consisting of hydrogen and lower alkyl, and R is hydrocarbyl or oxyhydrocarbyl of 1 to 14 carbon atoms, if oxyhydrocarbyl, containing 1 to 4 oxy groups, and may be either aliphatic or aryl, unsubstituted or substituted with one or more lower alkyl, amino, nitro or halogen moieties.

29 Claims, 3 Drawing Sheets

ORTHO AND THIO-ORTHO ESTER POLYMER

DESCRIPTION

1. Technical Field

The invention is in the field of ortho ester polymer chemistry and relates generally to novel polymers having thio ortho ester and/or sulfoxy ortho ester linkages. The invention also relates to bioerodible or biodegradable devices fabricated from the novel polymers and useful for dispensing beneficial agents.

2. Background Art

Interest in synthetic biodegradable polymers for the systemic delivery of therapeutic agents began in the early 1970's with the work of Yolles et al. on poly(lactic acid), poly(glycolic acid) and copolymers thereof. Since that time various other polymers have been made or investigated for such use.

U.S. Pat. Nos. 4,093,709 and 4,304,767 describe two types of biodegradable (or "bioerodible") ortho ester polymers. The polymers of U.S. Pat. No. 4,093,709 are the reaction products of an ortho ester (or ortho carbonate) such as 2,2-diethoxytetrahydrofuran with a diol such as 1,4-cyclohexane dicarbinol. The reaction is carried out at elevated temperature, under reduced pressures and requires a relatively long reaction time. Drug or other active agent is entrapped (dispersed) in the polymer and is released therefrom as the polymer biodegrades due to hydrolysis.

U.S. Pat. Nos. 4,093,709, 4,131,648, 4,138,344 and 4,180,646 describe biodegradable or bioerodible poly (ortho ester) polymers. These polymers are the reaction product of an ortho ester (or an ortho carbonate) such as 2,2-diethoxytetrahydrofuran with a diol such as 1,4-cyclohexanedicarbinol. The reaction must be carried out at elevated temperature, under reduced pressure and requires a relatively long reaction time. Drug or other active agent is dispersed in the polymer and is released therefrom as the polymer biodegrades due to hydrolysis of the labile linkages.

U.S. Pat. No. 4,304,767 describes another type of poly(ortho ester) which is made by reacting a polyol with a polyfunctional ketene acetal. However, because ortho ester linkages at body pH and temperature are relatively stable, their hydrolysis rate is slow and thus the release of therapeutic agents dispersed in the polymer is also slow. Therefore, to achieve therapeutically useful drug delivery rates, the hydrolysis of the polymer must be catalyzed by the addition of acidic excipients.

The polymers of the present invention are also prepared from a polyfunctional ketene acetal but provide thio-ortho ester and/or sulfoxy-ortho ester linkages as well as ortho ester linkages between the various mer units. Introduction of thio-ortho ester and sulfoxy-ortho ester groups between the various mer units provides a means for controlling the rate at which the polymer biodegrades and, therefore, the addition of acidic compounds to catalyze polymer hydrolysis rate is not necessary. This is a significant advantage. We have also found that the rate of hydrolysis of the novel sulfoxy-ortho ester linkage is much faster than the rate of hydrolysis of an ortho ester linkage, and that controlling the relative amounts of these two types of linkages between the various mer units also enables control over the rate at which the polymer biodegrades.

It is not possible to make the present polymers by the method described in U.S. Pat. No. 4,304,767, i.e., by reacting a polyol with a polyfunctional ketene acetal. In this regard, the present polymers are made by reacting a polyfunctional ketene acetal with polyfunctional carboxylic acids or monomers having one hydroxy and one or more carboxy groups.

A further substantial difference between polymers described in the present invention and those described in the '767 patent is that the present reaction between carboxylic acid groups and ketene acetals occurs spontaneously and thus requires no acid catalyst.

DISCLOSURE OF THE INVENTION

The present invention provides novel biodegradable polymers based on mono- and poly-thiols, a process for making those polymers, and biodegradable devices fabricated from the novel compounds and useful for delivering beneficial agents.

The polymers of the invention are characterized by containing at least one of the following mer units (I), (II), (III) or (IV):

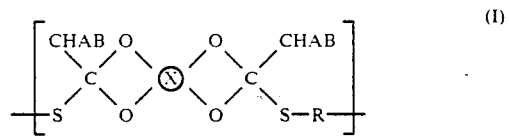

(I)

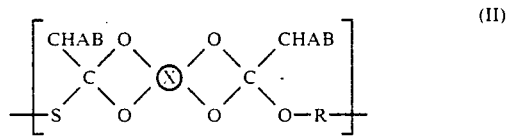

(II)

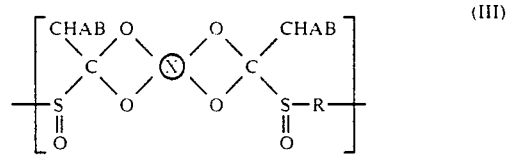

(III)

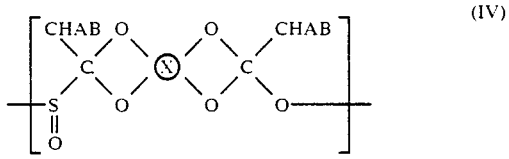

(IV)

where X is a quadrivalent organic grouping, A and B are hydrogen or lower alkyl and may be the same or different, and R is an alkyl, cycloalkyl or aryl moiety as will be described.

The process for making the polymers containing the mers of formulae (I) and/or (II) comprises catalytically reacting a polyfunctional ketene acetal such as a diketene acetal of formula (Va) or (Vb)

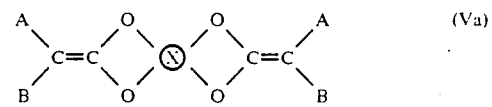

(Va)

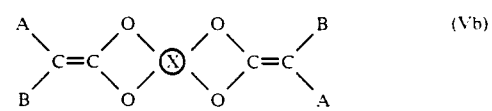

(Vb)

where X, A and B are as given above, with a mono- or polythiol of formula HS—R—SH or HS—R—OH, under anhydrous conditions, for a time sufficient to provide the desired polymeric product. Sulfoxy moieties (as in mer structures (III) and (IV)) may be provided by oxidizing the polymer product so obtained.

The biodegradable devices of the invention comprise bodies of a polymer containing mer units (I), (II), (III) and/or (IV) admixed with a beneficial agent or coated into a beneficial agent composition.

MODES FOR CARRYING OUT THE INVENTION

Figure 3:
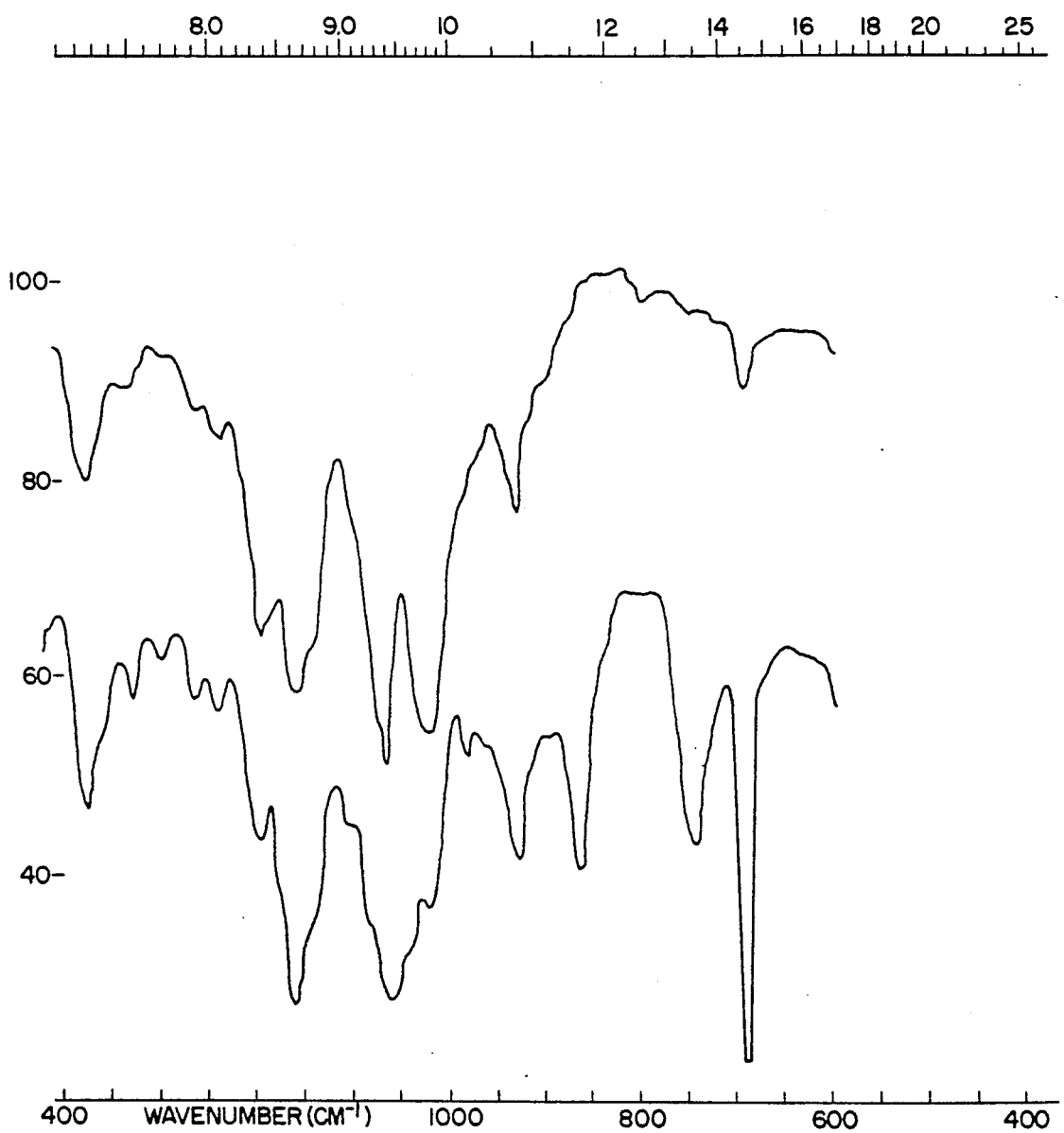
FIG. 3 is a section of the IR spectrum of the product obtained in Example 7.

The term "mer" intends the structurally recurring units or monomer units of the polymers of the invention. The mers of a given polymer may be the same or different, and when different, may be arranged in block or random fashion. When the mers of a polymer are the same, the polymer is called a homopolymer; when they are different, the polymer is called a copolymer.

The terms "biodegradable" and "bioerodible", as used herein to describe the novel polymers, intend solid, gel, or viscous polymers that completely solubilize as a consequence of hydrolysis.

The term "beneficial agent" as used herein intends a compound or composition of matter that provides a desired and useful effect upon the environment or individual (man or animal) to which it is administered. This term includes, without limitation, agents such as drugs, nutrients, plant growth regulants, pesticides, catalysts, disinfectants, and the like.

The term "drug" as used herein intends a compound or composition of matter which when administered to an individual (man or animal) induces a desired pharmacologic and/or physiologic effect by local and/or systemic action. In general, the term includes the therapeutic or prophylactic agents in all major therapeutic/prophylactic areas of medicine.

The term "effective amount" as used herein intends that quantity of agent that is required to provide the desired or intended beneficial effect without intolerable side effects, such as toxicity.

"Lower alkyl" as used herein is intended to mean a linear or branched alkyl substituent having 1 to 6 carbon atoms.

"Mono-thiol" intends a compound containing one —SH moiety, while "poly-thiol" intends a compound containing two or more —SH moieties.

The X grouping in the above formulae is a quadrivalent organic moiety which may be, for example, a tetravalent carbon atom, a neopentyl group, a tetra-substituted cyclohexyl species, or the like. A and B, as noted, are independently selected from the group consisting of hydrogen and lower alkyl.

The symbol R in the formulae represents a hydrocarbyl or oxyhydrocarbyl group of 1 to 14 carbon atoms, usually 2 to 9 carbon atoms. The number of oxy (—O—) groups in the oxyhydrocarbyl moiety will typically be 1 to 4. The hydrocarbyl group will preferably be saturated, branched- or straight-chain aliphatic or saturated cycloaliphatic, unsubstituted or substituted with one or more moieties which will not interfere with the polymerization reaction, e.g., lower alkyl, amino, nitro, halogen, or the like.

The R moieties may also be aryl, in which case they are preferably carbocyclic, and may be monocyclic or polycyclic (fused) of 2 to 4 rings, but will typically contain 1 or 2 rings, which may be unsubstituted or substituted as described above.

The number of repeating mer units in the polymer will normally be in the range of 2 to 1000, preferably 2 to 200, and most preferably 5 to 200.

Examples of suitable diketene acetals monomers are given in Table (I).

TABLE I

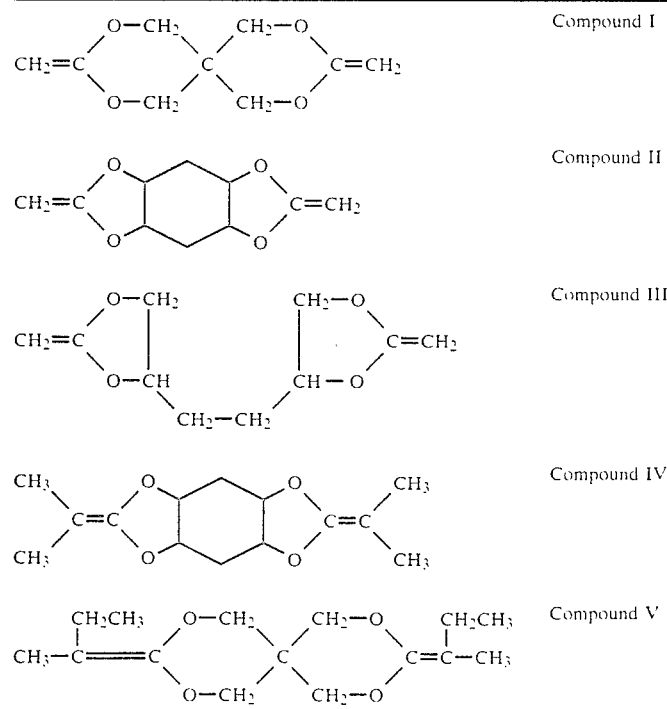

TABLE I-continued

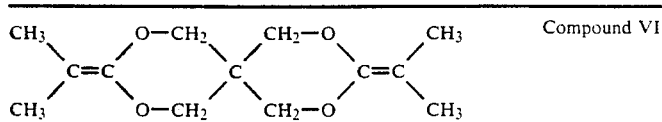
Compound VI

The thiol reactant HS—R—SH or HS—R—OH is preferably a mono- or poly-thiol in which the functional groups are on the terminal carbon atoms of aliphatic chains or are para with respect to each other in six-membered carbocyclic groups, or are terminal in linear polyesters or polyethers. Examples of thiol reactants include 1,6-hexanedithiol, trans-cyclohexanedimercaptomethane, bis-mercaptoethyl piperazine, 1,4-butanedithiol, 1,2-ethanedithiol, 1,6-hydroxymercaptohexane, 1,5-hydroxymercaptopentane, and cis-cyclohexanemethanolmercaptomethane.

The polymers are made via a condensation reaction between the selected diketene acetal and the mono- or poly-thiol (or both), under anhydrous conditions. Normally, the reaction between the poly-thiol and the diketene acetal does not require the use of a catalyst. However, when a hydroxy-thiol is used as one of the reactants, the use of a Bronsted catalyst is advantageous. Examples of suitable catalysts include p-toluenesulfonic acid and methanesulfonic acid.

The process may be carried out neat (no solvent) or in aprotic solvents such as tetrahydrofuran (THF), glyme (ethylene glycol dimethyl ether), diglyme, cymene, cumene, or chlorinated hydrocarbons. In either case, care should be taken to maintain anhydrous conditions. The reaction will normally be run at temperatures in the range of 20° to 150° C., preferably 20° to 75° C. The preferred approximate mol ratio of reactants (diketene acetal:mono- or poly-thiol) is about 3:2 to 2:3, more preferably about 1:1. While these ratios may be altered slightly, significant variation is not desirable as the molecular weight range of the product is dependent on the mol ratios of the reactants.

Scheme 1 illustrates reaction of the diketene acetal monomer (Va) with the di-thiol HS—R—SH according to the present invention:

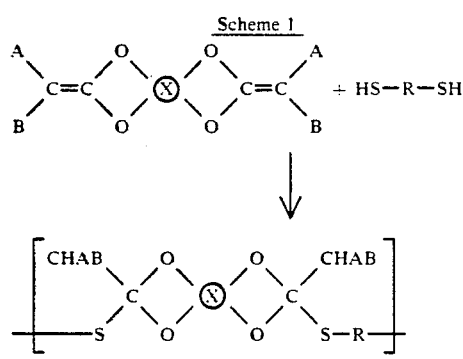

Scheme 2 illustrates reaction of the diketene acetal monomer (Va) with the mono-thiol HS—R—OH according to the present invention:

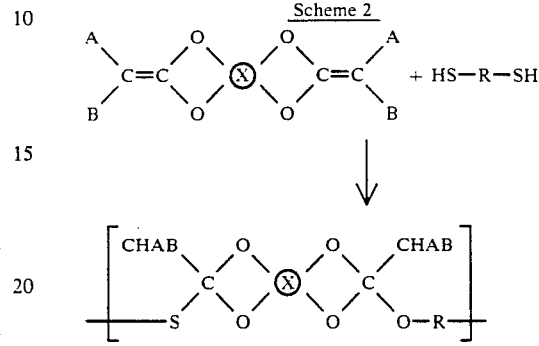

Either of the polymers so provided may then be oxidized or partially oxidized according to the method outlined in Scheme 3

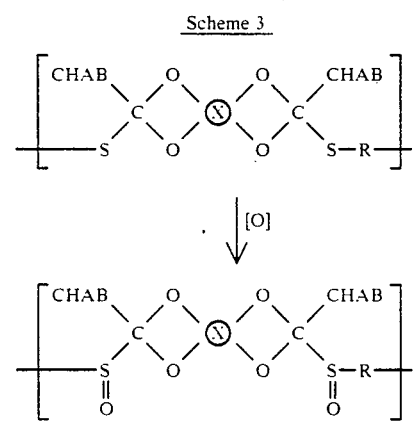

to give a corresponding polymer containing sulfoxy-ortho ester linkages. Oxidation of the thio ortho ester can be done with equivalent amounts of an oxidant such as m-chloro- or m-bromo-perbenzoic acid or ozone, in an organic solvent inert to oxidation, e.g., methylene chloride or chloroform. The oxidation can be run at temperatures in the range of 0° to 100° C. preferably at 0° to 50° C.

In an alternative embodiment, the reaction of the selected diketene acetal with the mono- or poly-thiol is carried out in the presence of a dicarboxylic acid HOOC—R—COOH, or a hydroxy-carboxylic acid HOOC—R—OH, with R as given above. The dicarboxylic acid or hydroxy-carboxylic acid is incorporated into the polymer in proportion to the amount present during polymerization.

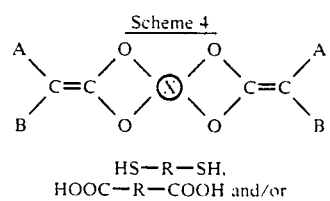

HS—R—SH,
HOOC—R—COOH and/or

-continued
Scheme 4

HOOC—R—OH

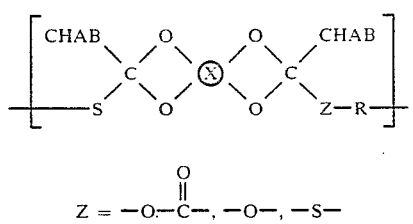

$$Z = -O-\overset{O}{\underset{\|}{C}}-, -O-, -S-$$

The following examples further illustrate the orthoester polymers of the invention and the process by which they may be prepared. These examples are not intended to limit the invention in any manner.

EXAMPLE 1

Under anhydrous conditions 5.60 g (0.0261 mole) of DETOSU and 3.50 g (0.0261 mole) of 1,6-hydroxymercaptohexane were weighed into a 100 ml round bottom flask. The mixture was dissolved in 10 ml of dry distilled tetrahydrofuran and while stirring by means of a magnetic stirring bar, 4 drops of p-toluene sulfonic acid solution in tetrahydrofuran (10 mg/ml) were added. Strict anhydrous conditions were maintained during stirring and catalyst addition. The addition reaction was highly exothermic and the boiling point of tetrahydrofuran was reached within 5 minutes. After about one hour, the solution temperature returned to room temperature. The polymer was isolated by precipitation into a large excess of methanol, isolated by filtration and dried in a vacuum oven.

The following polymer was obtained:

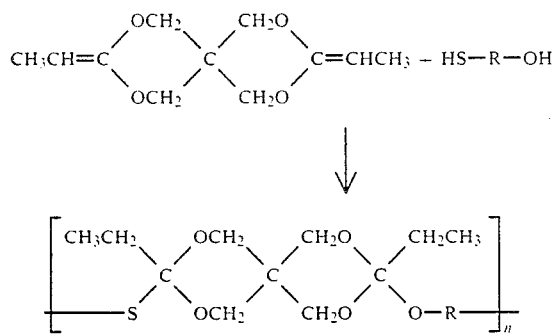

In this particular case, R was —(CH$_2$)$_6$—.

GPC analysis gave a weight average molecular weight of 25,000.

EXAMPLE 2

Using the same conditions as in Example 1, 10.31 g (0.0486 mole) of DETOSU and 8.57 g (0.0486 mole) of trans-cyclohexanedimercaptomethane were dissolved in 30 ml of dry distilled tetrahydrofuran. After stirring for 1 hr, the polymer was isolated by precipitation into a large excess of methanol, isolated by filtration and dried in a vacuum oven.

In this particular example R has the following structure:

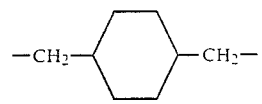

Figure 1:
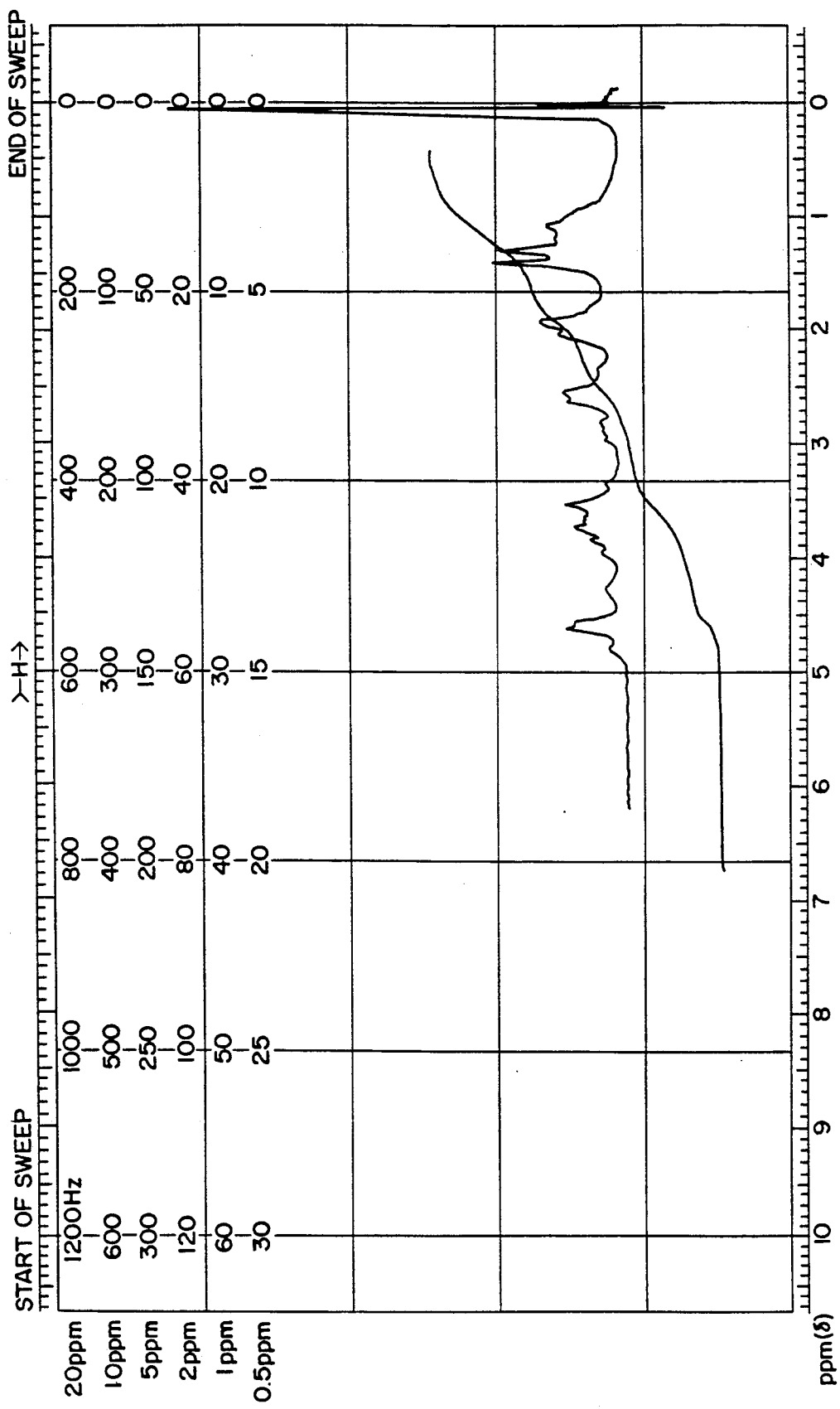

The product was characterized by $^1$H NMR spectroscopy. The NMR spectrum is shown in FIG. 1. The weight average molecular weight was determined by gel permeation chromatography (GPC) to be 96,000.

EXAMPLE 3

Using the same conditions as in Example 1, 4.25 g (0.02 mole) of DETOSU and 4.12 g (0.02 mole) of bismercaptoethyl piperazine were dissolved in 15 ml of dry distilled tetrahydrofuran and the solution was heated at 65° C. for 3 hr. The polymer was isolated as described under Example 1.

In this particular example, R had the following structure:

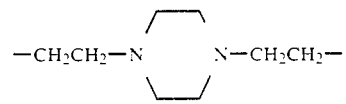

Figure 2:
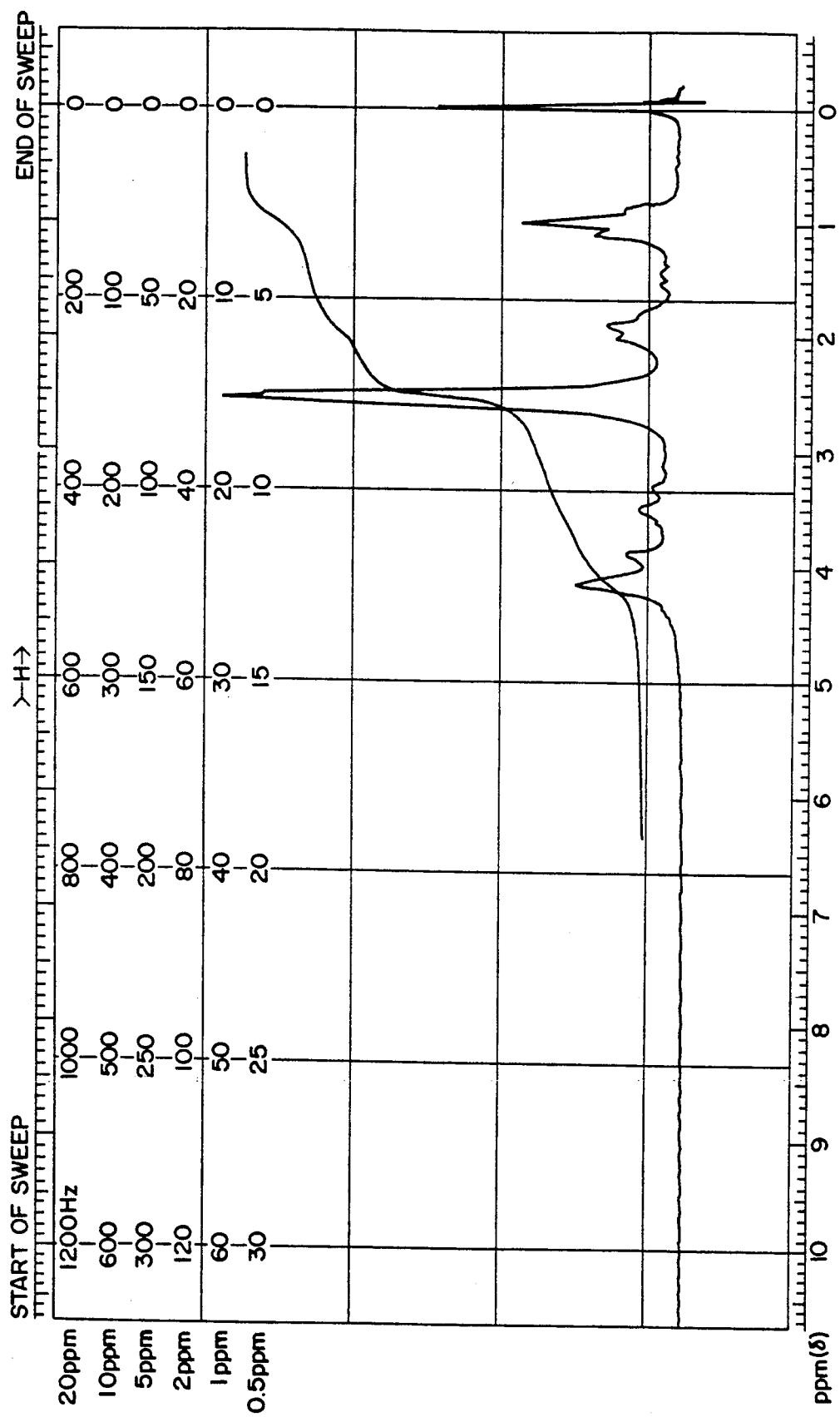
FIGS. 1 and 2 are the $^1$H NMR spectra of the products obtained in Examples 1 and 2, respectively.

The weight average molecular weight determined by GPC was 36,000 D. The $^1$H NMR spectrum of the polymer is shown in FIG. 2.

EXAMPLE 4

Under anhydrous conditions 5.60 g (0.0261 mole) of 3,9-bis(ethylene)2,6,8,10-tetraoxaspiro[5.5]undecane (DETOSU) and 4.05 g (0.0261 mole) of 1,6-hexanedithiol were weighed into a 100 ml round bottom flask. The mixture was dissolved in 10 ml of dry distilled tetrahydrofuran and stirred by means of a magnetic stirring bar. Anhydrous conditions were maintained during stirring. The addition reaction was highly exothermic and the boiling point of tetrahydrofuran was reached within 5 minutes. After about one hour, the solution temperature returned to room temperature. The polymer was isolated as described in Example 1.

The following polymer was obtained:

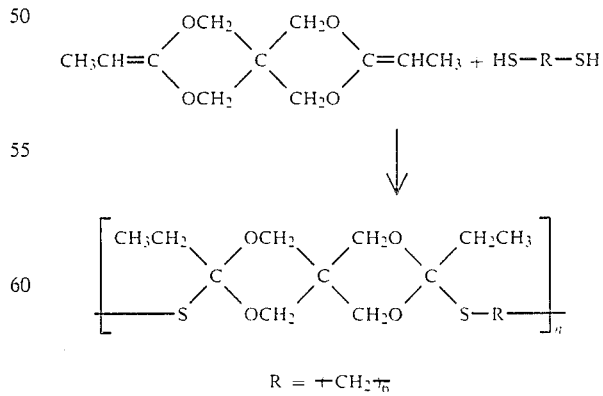

The weight average molecular weight obtained by gel permeation chromatography using polystyrene standards was 30,000 D.

EXAMPLE 5

Following a procedure identical to that described under Example 1, 4.25 g (0.02 mole) of DETOSU are reacted with 2.44 g (0.02 mole) of 1,4-butanedithiol. In this particular case, R is $-(CH_2)_4-$.

EXAMPLE 6

Following a procedure identical to that described under Example 1, 4.25 g (0.02 mole) of DETOSU are reacted with 1.88 g (0.02 mole) of 1,2-ethanedithiol. In this particular case, R is $-(CH_2)_2-$.

EXAMPLE 7

A monothio ortho ester was first prepared by reacting 10.31 g (0.0486 mole) of DETOSU and 8.57 g (0.0486 mole) of trans-cyclohexanedimercaptomethane. Then, 1.94 g (0.01 equivalents of S) of that polymer were dissolved in 20 ml of methylene chloride. The solution was then cooled in an ice-bath and 2.15 g (about 0.01 mole) of 80-85% m-chloro perbenzoic acid in 20 ml methylene chloride was added dropwise. The reaction mixture was then stirred under argon for 18 hr, filtered and the filtrate washed three times with 25 ml portions of a saturated sodium bicarbonate solution. The organic layer was separated and dried over anhydrous magnesium sulfate and then evaporated to dryness.

The following polymer was obtained

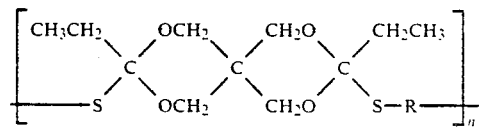

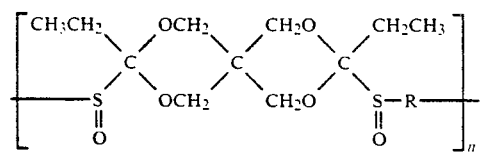

In this particular case R had the following structure:

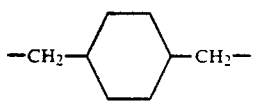

A section of the IR spectrum of the product, along with that of the starting polymer, is shown in FIG. 3.

EXAMPLE 8

A monothio ortho ester was first prepared by reacting 10.31 g (0.0486 mole) of DETOSU with 7.30 g (0.0486 mole) of 1,6-dithiohexane. Then, 1.81 g (0.01 equivalents of S) were dissolved in methylene chloride. The solution was cooled in an acetone/dry ice bath and ozone was bubbled through the solution for 5 minutes. The solution was then stirred at room temperature for 2 hr. The oxidized product was isolated by evaporation of the solvent. In this particular case R was $-(CH_2)_6-$.

The devices of the invention for dispensing beneficial agents may be made by mixing (dispersing) the beneficial agent (e.g., drug) with the polymer to form a homogeneous dispersion of polymer and agent and forming the dispersion into the desired shape or by coating a body of beneficial agent composition with the polymer. Both of these techniques of making biodegradable sustained-release devices have been described with respect to other orthoester polymers (see, for instance, U.S. Pat. No. 4,093,709) and thus do not need to be reiterated.

Modification of the above-described modes for carrying out the invention that are obvious to those of skill in the fields of polymer chemistry and sustained release dispensers are intended to be within the scope of the following claims.

We claim:

1. An ortho ester polymer containing a combination of the following mer units (I), (II), (III) or (IV):

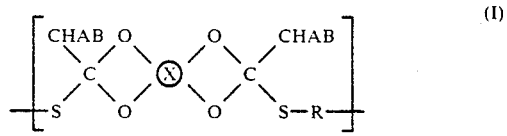

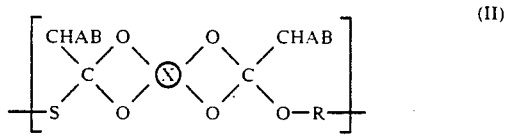

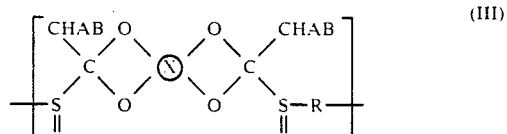

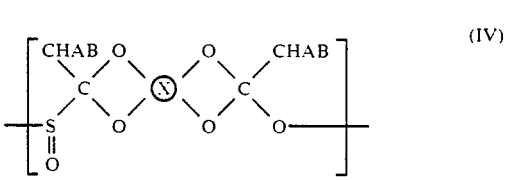

wherein X is a quadrivalent organic grouping, A and B are independently selected from the group consisting of hydrogen and lower alkyl, and R is hydrocarbylene or oxyhydrocarbylene of 1 to 14 carbon atoms, when oxyhydrocarbylene, containing 1 to 4 oxy groups, and are either aliphatic or aryl, unsubstituted or substituted with one or more lower alkyl, amino, nitro or halogen moieties.

2. The polymer of claim 1, wherein R is hydrocarbyl of 2-9 carbon atoms.

3. The polymer of claim 1, wherein X is a tetravalent carbon atom.

4. The polymer of claim 1, wherein X is neopentyl.

5. The polymer of claim 1, wherein X is cyclohexyl.

6. The polymer of claim 1, wherein R is phenyl.

7. The polymer of claim 1, wherein R is cyclohexyl.

8. The polymer of claim 1, wherein R is lower alkyl.

9. The polymer of claim 1, wherein the number of mer units in the polymer is in the range of 5 to 200.

10. A bioerodible polymer containing the mer unit

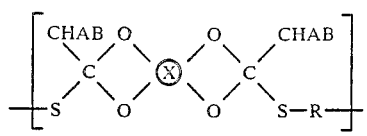
(I)

wherein X is a quadrivalent organic grouping, A and B are independently selected from the group consisting of hydrogen and lower alkyl, and R is hydrocarbylene or oxyhydrocarbylene of 1 to 14 carbon atoms, when oxyhydrocarbylene, containing 1 to 4 oxy groups, and are either aliphatic or aryl, unsubstituted or substituted with one or more lower alkyl, amino, nitro or halogen moieties.

11. A bioerodible polymer containing the mer unit

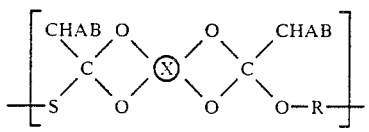
(II)

wherein X is a quadrivalent organic grouping, A and B are independently selected from the group consisting of hydrogen and lower alkyl, and R is hydrocarbylene or oxyhydrocarbylene of 1 to 14 carbon atoms, when oxyhydrocarbylene, containing 1 to 4 oxy groups, and are either aliphatic or aryl, unsubstituted or substituted with one or more lower alkyl, amino, nitro or halogen moieties.

12. A bioerodible polymer containing the mer unit

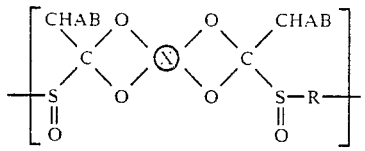
(III)

wherein X is a quadrivalent organic grouping, A and B are independently selected from the group consisting of hydrogen and lower alkyl, and R is hydrocarbylene or oxyhydrocarbylene of 1 to 14 carbon atoms, when oxyhydrocarbylene, containing 1 to 4 oxy groups, and are either aliphatic or aryl, unsubstituted or substituted with one or more lower alkyl, amino, nitro or halogen moieties.

13. A bioerodible polymer containing the mer unit

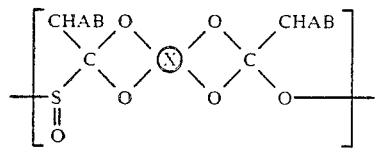
(IV)

wherein X is a quadrivalent organic grouping and A and B are independently selected from the group consisting of hydrogen and lower alkyl.

14. A method for preparing a polymer according to claim 1, and containing mer units (I) or (II) or both, comprising reacting a diketene acetal represented by (Va) or (Vb)

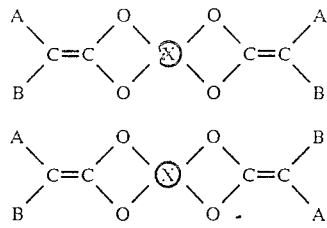
(Va)
(Vb)

wherein X is a quadrivalent organic grouping and A and B are independently selected from the group consisting of hydrogen and lower alkyl, with a mono- or poly-thiol or both under anhydrous conditions.

15. The method of claim 14, wherein the monothiol is represented by the formula HS—R—OH, in which R is hydrocarbyl or oxyhydrocarbyl of 1 to 14 carbon atoms, when oxyhydrocarbyl, containing 1 to 4 oxy groups, and is either aliphatic or aryl, unsubstituted or substituted with one or more lower alkyl, amino, nitro or halogen moieties.

16. The method of claim 14 wherein the polythiol is represented by HS—R—SH, in which R is hydrocarbylene or oxyhydrocarbylene of 1 to 14 carbon atoms, when oxyhydrocarbylene, containing 1 to 4 oxy groups, and is either aliphatic or aryl, unsubstituted or substituted with one or more lower alkyl, amino, nitro or halogen moieties.

17. The method of claim 14, wherein the reaction is carried out in the presence of a dicarboxylic acid reactant.

18. The method of claim 17, wherein the dicarboxylic acid reactant is represented by the structure HOOC—R—COOH, wherein R is hydrocarbylene or oxyhydrocarbylene of 1 to 14 carbon atoms, when oxyhydrocarbylene, containing 1 to 4 oxy groups, and is either aliphatic or aryl, unsubstituted or substituted with one or more lower alkyl, amino, nitro or halogen moieties.

19. The method of claim 14, wherein the reaction is carried out neat.

20. The method of claim 14, wherein the reaction is carried out in an aprotic solvent.

21. The method of claim 14, wherein after reacting the diketene acetal with the mono- or poly-thiol or both, the polymer is oxidized to contain one or more mer units represented by the formula

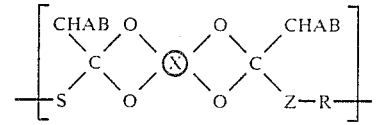

wherein Z is selected from the group consisting of

22. The method of claim 14, carried out in the presence of a Bronsted acid catalyst.

23. The method of claim 14, wherein the Bronsted acid catalyst is p-toluenesulfonic acid or methanesulfonic acid.

24. The method of claim 14, wherein the approximate mol ratio of diketene acetal to thiol is about 2:3 to 3:2.

25. The method of claim 14, wherein the approximate mol ratio of diketene acetal to thiol is about 1:1.
26. The method of claim 21, wherein Z is
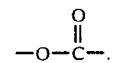
27. The method of claim 21, wherein Z is —S—.
28. The method of claim 21, wherein Z is —O—.
29. A biodegradable beneficial agent dispenser comprising the polymer of claim 1.
* * * * *